United States Patent
Murphy et al.

[11] Patent Number: 5,861,524
[45] Date of Patent: Jan. 19, 1999

[54] OLIGOMERIC FLUOROALKYLSILOXANES AS OIL SPREADING AGENTS

[75] Inventors: Gerald J. Murphy, Hopewell Junction, N.Y.; Seisaku Kumai, Fujisawa, Japan; Jeffrey A. Cooke, Peekskill, N.Y.; Yutaka Furukawa, Asahi-ku, Japan; George A. Policello, Ossining, N.Y.

[73] Assignee: OSi Specialties, Inc., Greenwich, Conn.

[21] Appl. No.: 844,810

[22] Filed: Apr. 22, 1997

Related U.S. Application Data

[60] Provisional application No. 60/015,881, Apr. 22, 1996.

[51] Int. Cl.$^6$ .......................................................... C07F 7/08
[52] U.S. Cl. .......................... 556/445; 556/454; 556/456; 504/116; 424/84; 424/407; 424/DIG. 8; 252/175; 252/351; 252/358
[58] Field of Search ..................................... 552/445, 454, 552/456; 504/116; 424/407, 84, DIG. 8; 252/175, 351, 358

[56] References Cited

U.S. PATENT DOCUMENTS

| | | |
|---|---|---|
| 3,607,899 | 9/1971 | Brown et al. ............................. 556/454 |
| 3,660,453 | 5/1972 | Groenhof et al. ....................... 556/454 |
| 4,171,267 | 10/1979 | McAfee et al. . |
| 4,514,319 | 4/1985 | Kulkarni et al. . |
| 4,968,828 | 11/1990 | Yamamoto . |
| 5,047,491 | 9/1991 | Saho et al. . |
| 5,446,114 | 8/1995 | O'Lenick Jr. . |

FOREIGN PATENT DOCUMENTS

| | | |
|---|---|---|
| 648 413 A1 | 4/1995 | European Pat. Off. . |
| 7-53719 | 2/1995 | Japan . |

OTHER PUBLICATIONS

McCall et al., "Modeling the Foliar Behvior of Atrazine with and without Crop Oil concentrate on Giant Foxtail and the Effect of Tridiphane on the Model Rate Constants", *J. Agric, Food Chem.*, vol. 34, pp. 235–238 (1986).

*Primary Examiner*—Paul F. Shaver
*Attorney, Agent, or Firm*—Edward K. Welch, II; Andrew S. Reiskind; Timothy X. Witkowski

[57] ABSTRACT

Oligomeric fluoroalkylsiloxanes corresponding to the formula:

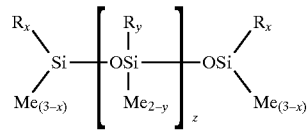

wherein x is 0 to 3, y is 0, 1, or 2; z is 0 or 1; x+y>0, and R has the formula $-C_aH_{2a}-O_b-C_dH_{2c}-C_dF_{2d+1}$ in which a is 2–4, b is 0 or 1, c is 0–8 and d is 4–12, and compositions thereof with an oil, are useful as spreading agents and in agricultural applications.

29 Claims, 1 Drawing Sheet

OLIGOMERIC FLUOROALKYLSILOXANES AS OIL SPREADING AGENTS

This application claims priority from U.S. Provisional application Ser. No. 60/015,881, filed Apr. 22, 1996.

FIELD OF THE INVENTION

The present invention relates to oligomeric fluoroalkylsiloxanes. Fluoroalkyl-modified polysiloxanes are known to impart water and oil repellency to surfaces and substances to which they are applied or incorporated. In addition, these compounds are known to show lubricating, anti-biofouling and anti-graffiti properties. We have found that a particular class of fluoroalkylsiloxanes, namely fluoroalkyidisiloxanes and fluoroalkyltrisiloxanes, exhibit especially favorable spreading characteristics, and that these characteristics can be taken advantage of by the use of the compounds as oil-spreading agents, oil- and water-repellent coatings and surface lubricants. The present invention thus discloses fluoroalkyl-substituted disiloxanes and trisiloxanes and a general method for preparing them.

BACKGROUND OF THE INVENTION

Many useful oil-based agricultural chemicals are less effective than desired because they do not spread well. It is typical to apply oil-based chemicals using a carrier such as animal, vegetable, or paraffin oils or to apply dormant oils as aqueous sprays. The bulk surface tension of a liquid plays a key role in its ability to spread on hydrophobic surfaces such as the waxy cuticle of a leaf or the exoskeleton of an arthropod. If the surface tension of a liquid is not sufficiently low, the droplet will not spread effectively. Thus, there is a need for adjuvants which reduce the surface tension of lipophilic liquids and, thereby, increase the effectiveness of oil-based agricultural chemicals.

The use of oils as adjuvants or carriers for agricultural applications is well known. Paraffinic, animal and vegetable oils have been used in formulations for dormant spray oils, in preparations for the management of insects and mites including oils that suffocate arthropod pests by clogging their spiracles, in crop oil concentrates and crop oils, and in emulsifiable concentrates. One of the effects of the oil is to increase the penetration of pesticides into the target organism. In addition, the oils often enhance spreading on target surfaces, which increases the effectiveness of the pesticide being applied.

According to P. J. McCall, et al. (*J. Agric. Food Chem.*, 34(2), 235-8), the addition of a crop oil concentrate (COC) to atrazine spray solutions significantly increased the amount of pesticide absorbed by giant foxtail sprayed with the chemical. Typically, 30% of the applied chemical penetrated the leaf in the presence of COC, while only 10% penetrated without COC. Kulkarni, et al (U.S. Pat. No. 4,514,319) disclosed relatively high molecular weight lipophilically modified silicones that, when used in connection with organosilicone surfactants, reduced the surface tension of hydrocarbon oils containing hydrophobic fillers, thus providing high efficiency antifoam compositions. EP 648413 A, to Murphy, et a., discloses the use of alkyltrisiloxanes as spreading agents for agricultural oils.

U.S. Pat. No. 4,171,267 to McAfee, et al, disclosed an organopolysiloxane fluid as a component of a miscible composition for lubricating organic fibers that contained a hydrocarbon oil and a bridging agent obtained by reacting an organopolysiloxane with a long chain alcohol.

Fluoroalkyl-substituted polysiloxanes are also known in the art, and have been used to modify the surface characteristics of a substrate, usually providing water and/or oil repellency or lubrication.

For example, JP 07-053719 illustrates a process for preparing fluoroalkylpolysiloxanes by hydrosilation with a corresponding polysiloxane containing $MeSi(H)O_{2/2}$ units. Yamamoto, et al., (U.S. Pat. No. 4,968,828) demonstrate the preparation of disiloxanes containing both terminal fluoroalkyl and SiH moieties, useful as a modifier for improving the surface properties of various materials. Saho, etal., (U.S. Pat. No. 5,047,449) demonstrate a process for the preparation of polysiloxanes endcapped with fluoroalkyl and polyether substituents. O'Lenick (U.S. Pat. No. 5,446,114) demonstrates the synthesis of fluorinated dimethicone copolyols which pass water and air but not oil when applied to textiles.

SUMMARY OF THE INVENTION

The novel, symmetrical, oligomeric fluoroalkylsiloxanes of the present invention have the general structure of Formula (I):

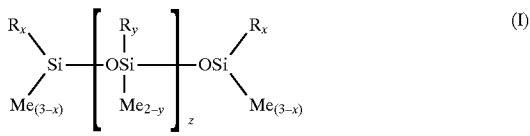

wherein x is 0 to 3, y is 0, 1, or 2; z is 0 or 1; x+y>0, and R has the formula—$CaH_{2a}$—$O_b$—$C_cH_{2c}$—$C_dF_{2d+1}$ in which a is 2–4, b is 0–1, c is 0–8 and d is 4–12 preferably a=2 or 3, b=0 or 1, c=0–3 and d=6–8; most preferably a=3, b=0, c=0 and d=8, or a=3, b=1, c=3 and d=8.

Representative examples of the fluoroalkyltrisiloxanes (II) and fluoroalkyldisiloxanes (III) of the present invention are also illustrated.

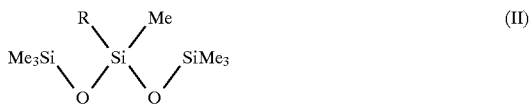

wherein R is as defined above.

Another aspect of the present invention is compositions, useful for instance in agricultural applications, comprising about 0.1% by weight to about 99.9% by weight of a fluoroalkylsiloxane of formula (1) and about 99.9% by weight to about 0.1% by weight of an oil.

Another aspect of the present invention is a method of enhancing the spreading of vegetable, animal or paraffinic oil, comprising incorporating into the oil a fluoroalkylsiloxane of formula (I) or composition as aforementioned of a fluoroalkylsiloxane and oil.

Another aspect of the present invention is a method of treating a plant or arthropod with an oil-containing composition, comprising applying to a plant or arthropod a composition comprising from about 0.1% by weight to about 99.9% by weight of an oil and about 99.9% by weight to about 0.1% by weight of a fluoroalkylsiloxane of formula (I).

Another aspect of the present invention is a process for improving the efficacy of an oil soluble pesticide, comprising combining with the pesticide a fluoroalkylsiloxane of formula (I) or a composition as aforementioned of a fluoroalkylsiloxane of formula (I) and an oil.

DETAILED DESCRIPTION OF THE INVENTION

Figure 1:
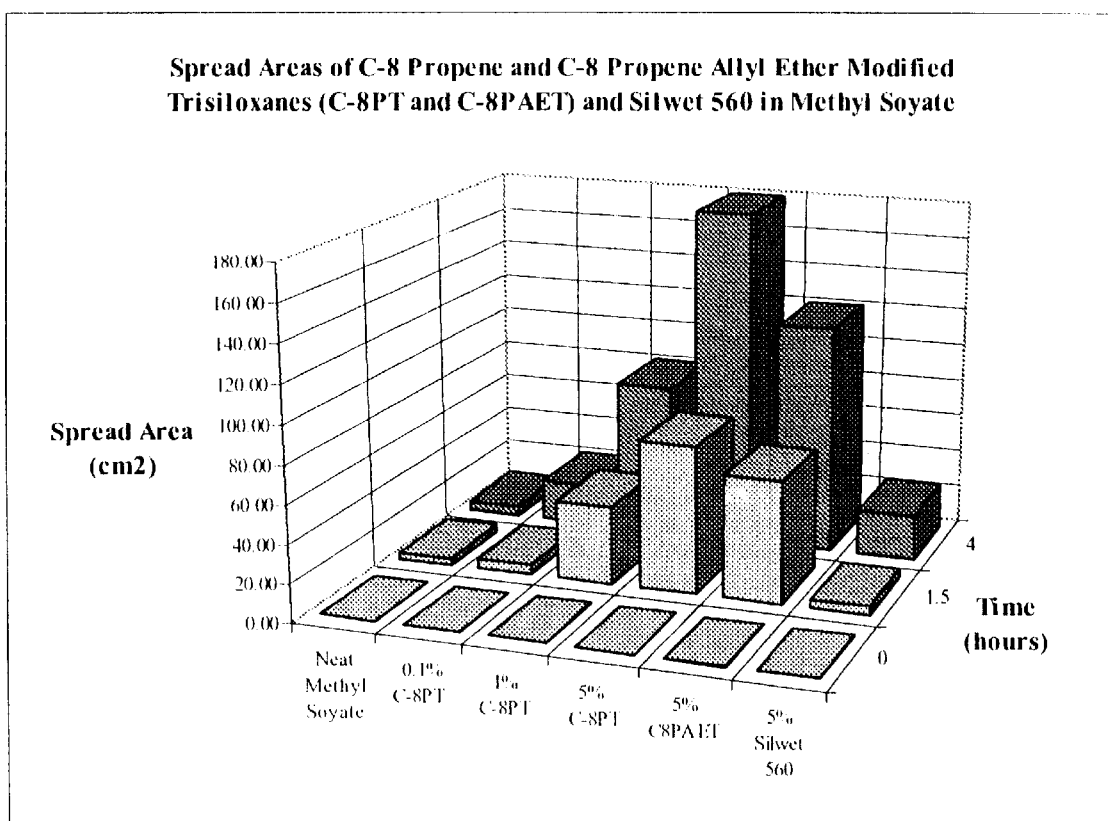
FIG. 1 is a graphic representation of the data obtained in Example 5 and presented in Table 1.

The present invention provides novel fluoroalkyldisiloxanes and fluoroalkyltrisiloxanes that are useful as spreading agents when incorporated in a mixture of about 0.1% to about 99.9% of a vegetable, animal or paraffinic oil carrier, such as methylated or ethylated seed oil. The composition displays a marked improvement in spreading relative to the carrier oil alone and has utility in, for example, improving the efficiency of applying pesticides to agricultural products.

The carrier oil of the invention, which is present from about 99.9 to about 0.1 weight percent of the composition (and preferably more than 80 weight percent of the composition with the fluoroalkylsiloxane comprising less than 20 weight percent of the composition) is comprised of oils or mixtures thereof, selected from paraffinic, isoparaffinic, cycloparaffinic and naphthenic mineral oils, vegetable oils, such as soybean oil, canola oil, castor oil, palm oil, olive oil, corn oil, cottonseed oil, sesame seed oil and the like. In addition, esterified oils, such as methylated soybean oil, methyl palmitate, methyl oleate, ethylated seed oils, and the like are also suitable carrier oils. Mixtures of mineral, vegetable and/or esterified oils may also be employed. The carrier oil may itself be an active ingredient, e.g., a pesticide.

Exemplary mineral oils are those marketed under the trade names EXXOL®, ISOPAR®, NORPAR® and ORCHEX® from Exxon Chemical (Houston, Tex.). Methylated oils such as the methylated soybean oil are available from Henkel, Canada, under the product name "Emery 2235, Distilled Methylsoyate." One skilled in the art would be able to determine other suitable oils from this listing.

Optionally, the composition can include a nonionic surfactant that is present from about 1 to about 50% by weight. Examples of suitable nonionic surfactants are those that are soluble in the fluoroalkyldisiloxane or fluoroalkyltrisiloxane/carrier oil matrix, and having an HLB between 8 and 17, for example, branched tridecyl alcohol ethoxylate. When the composition contains the optional ingredients, the fluoroalkyldisiloxane or fluoroalkyltrisiloxane/carrier oil mixture makes up the balance of the composition, with the ratio of the fluoroalkyldisiloxane or fluoroalkyltrisiloxane/carrier oil portion 99:1 to 1:99. Other optional ingredients are pesticides, as discussed below.

The composition is prepared by combining the components in the desired ratio, consistent with the guidelines described above, and mixing these ingredients according to conventional methods that will provide a clear to slightly hazy, uniform product. Mixing by a mechanical agitator or a mechanical shaker are examples of such methods. When the optional filler is included in the composition the ingredients are combined using a high shear mixer, such as a Lightnin' mixer.

The fluoroalkyldisiloxanes and fluoroalkyltrisiloxanes are useful as spreading agents for oil-based adjuvants such as crop oil concentrates, dormant oils, and non-aqueous, ultra-low volume oil sprays, where the pesticide is dispersed or dissolved in the carrier oil. In addition, the fluoroalkyldisiloxanes and fluoroalkyltrisiloxanes of the present invention are useful as spreading agents when incorporated into oil-based pesticide formulations, such as emulsifiable concentrates. The fluoroalkyldisiloxanes and fluoroalkyltrisiloxane compounds of this invention promote the spreading of the carrier oil or oil soluble pesticides on plant and/or arthropod surfaces.

By "pesticide" is meant any compound used to destroy pests, including herbicides, fungicides, insecticides, rodenticides, and the like. The term specifically includes oily materials not otherwise toxic, material used as pesticides in the destruction of aphids, scale insects, weeds, and the like. Illustrative examples of pesticides which can be employed include, but are not limited to, growth regulators, photosynthesis inhibitors, pigment inhibitors, mitotic disrupters, lipid biosynthesis inhibitors, cell wall inhibitors, and cell membrane disrupters. The amount of pesticide employed in compositions of the invention varies with the type of pesticide employed.

More specific examples of pesticide compounds that can be used in the compositions of the invention are: phenoxy acetic acids, phenoxy propionic acids, phenoxy butyric acids, benzoic acids, triazines and s-triazines, substituted ureas, uracils, bentazon, desmedipham, methazole, phenmedipham, pyridate, amitrole, clomazone, fluridone, norflurazone, dinitroanilines, isopropalin, oryzalin, pendimethalin, prodiamine, trifluralin, glyphosate, sulfonylureas, imidazolinones, clethodim, diclofop-methyl, fenoxaprop-ethyl, fluazifop-p-butyl, haloxyfop-methyl, quizalofop, sethoxydim, dichlobenil, isoxaben, and bipyridylium compounds.

The present invention also provides novel fluoroalkyldisiloxanes and fluoroalkyltrisiloxanes that are useful for imparting lubricity and/or oil and water repellency when applied to a substrate such as, but not limited to a metal surface or textiles. The fluoroalkyldisiloxanes and fluoroalkyltrisiloxanes may be applied alone, or in a composition with a suitable carrier, such as tetrachloroethylene. The enhanced spreading properties of the fluoroalkyldisiloxanes and fluoroalkyltrisiloxanes will increase the coverage on the surface, providing more rapid spreading and more efficient use of the compound.

Manufacture

The fluoroalkyldisiloxanes and fluoroalkyltrisiloxanes are synthesized most preferably by hydrosilation of a fluoroalkyl-modified olefin of the general structure $C_aH_{2a-1}O_bC_cH_{2c}C_dF_{2d+1}$ where a=2–5; b=0,1; c=0–8; d=4–12. Such fluoroalkyl-modified olefins can be synthesized using synthetic techniques familiar to organic chemists. The hydrosilation is performed with the precursors, such as, $Me_3SiOMeSi(H)OSiMe_3$ (1,1,1,3,5,5,5-heptamethyltrisiloxane) to make a fluoroalkyltrisiloxane, and with $HMe_2Si-O-SiMe_2H$ (1,1,3,3-tetramethyldisiloxane) to make a fluoroalkyldisiloxane (both precursors are available commercially, for example, from Aldrich Chemical Company, Milwaukee, Wis.). The reaction is catalyzed by standard hydrosilation catalysts, such as chloroplatinic acid, and may be conducted in the presence or absence of compatibilizing solvents, such as toluene.

Alternatively, the fluoroalkyltrisiloxanes can be prepared by reaction of a 1:2 (molar) mixture of a dichlorofluoroalkylmethylsilane with chlorotrimethylsilane in the presence of aqueous acid. The chlorosilane groups hydrolyze to the corresponding silanols, and then condense to yield a mixture of polysiloxanes. This mixture can subsequently be equilibrated once the water is removed, using standard equilibration catalysts such as sulfuric or trifluoromethanesulfonic acid. The product is a mixture of siloxanes with an average structure corresponding to the desired trisiloxane structure. The specific fluoroalkyltrisiloxane can, if desired, be isolated from the mixture, using standard techniques of organic chemistry, such as distillation.

The aforementioned reaction scheme can be illustrated as follows:

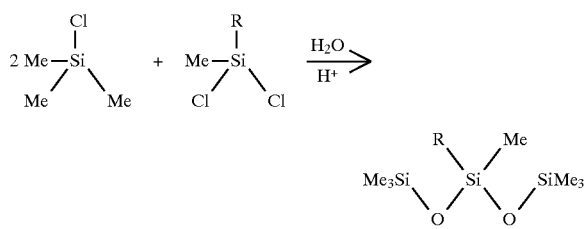

wherein R is a fluorine-containing substituent as defined previously.

An alternate synthetic route to the fluoroalkyldisiloxane involves the reaction of the chlorodimethylfluoroalkylsilane with aqueous acid to form the corresponding silanol, which subsequently condenses in the presence of an acidic catalyst to form the desired fluoroalkyl-modified disiloxane.

Uses

The present invention provides novel fluoroalkyl-modified oligomeric siloxanes that are useful as spreading agents when incorporated in a mixture of about 0.1% to about 99.9% of a vegetable, animal, silicone or paraffinic oil carrier, such as, methylated soybean oil. These compositions display a marked improvement in spreading relative to the carrier oil alone and has utility in, for example, improving the efficiency of applying pesticides to agricultural products.

The present invention also provides novel fluoroalkyldisiloxanes and fluoroalkyltrisiloxanes that are useful for providing a water and oil repellent coating on surfaces such as glass or metal, or on textiles. The disclosed fluoroalkyl-modified oligomeric siloxanes also find utility in lubrication of surfaces and as release agents. The enhanced spreading of these products augments their utility when used in such applications. The disclosed fluoroalkyldisiloxanes and fluoroalkyltrisiloxanes can be incorporated into coating formulations, resulting in more rapid spreading of the formulation prior to the curing of the coating and greater lubricity of the final cured surface.

EXAMPLES

Example 1

Hydrosilation of $C_3H_5C_8F_{17}$ with $Me_3SiOMeSi(H)OSiMe_3$ to yield: $Me_3SiOMeSi(C_3H_6C_8F_{17})OSiMe_3$:

$C_3H_5C_8F_{17}$ (40.0 g, 0.0869 mol) and $Me_3SiOMeSi(H)OSiMe_3$ (183.9 g, 0.8265 mol) were charged to a nitrogen flushed 1L round bottom flask equipped with a heating mantle, condenser, addition funnel, thermometer, mechanical stirrer, and nitrogen inlet. The mixture was stirred and heated to 80° C., at which time 1% chloroplatinic acid solution in isopropanol (0.43 mL, 10 ppm) was added via syringe. The temperature of the faint yellow solution rose to 87° C. over 6 minutes. After the initial exotherm subsided, the temperature was adjusted to 95° C., and the balance of the $C_3H_5C_8F_{17}$ (359.9 g, 0.7822 mol) added dropwise over 1 hour, ensuring that the temperature did not rise above 100° C. After the addition was complete, the light yellow clear solution was stirred an additional hour at 95° C., during which time the solution developed a darker color. Analysis indicated complete absence of Si-H groups. The reaction was cooled to 70° C., and NaHCO₃ (30 g) was added, and the suspension stirred 1 hour at this temperature. The reaction mixture was then filtered and stripped (rotary evaporator, 70° C., 1 mm Hg) to yield a clear, colorless, low viscosity liquid, identified as $Me_3SiOMeSi(C_3H_6C_8F_{17})OSiMe_3$.

Example 2

Hydrosilation of $C_3H_5OC_3H_6C_8F_{17}$ with $Me_3SiOMeSi(H)OSiMe_3$ to yield $Me_3SiOMeSi(C_3H_6OC_3H_6C_8F_{17})OSiMe_3$:

$C_3H_5OC_3H_6C_8F_{17}$ (51.3 g, 0.099 mol) and $Me_3SiOMeSiHOSiMe_3$ (20.4 g, 0.094 mol) were charged to a nitrogen flushed 250 mL round bottom flask equipped with a heating mantle, condenser, addition funnel, thermometer, mechanical stirrer, and nitrogen inlet. The mixture was stirred and heated to 85° C., at which time 1% chloroplatinic acid solution in isopropanol (0.05 mL, 10 ppm) was added via syringe. The temperature of the solution quickly rose to 145° C. over a period of one minute. After the initial exotherm subsided, the temperature of the reaction was maintained at 95° C. for a period of one hour. Analysis indicated complete absence of Si-H groups. The reaction was cooled to 70° C., and NaHCO₃ (5 g) was added, and the suspension stirred for 1 hour at this temperature. The reaction mixture was filtered and stripped (rotary evaporator, 70° C., 1 mm Hg) to yield a clear, colorless, low viscosity liquid, identified as a 10:1 mixture of $Me_3SiOMeSi(C_3H_6OC_3H_6C_8F_{17})OSiMe_3$ and excess, unreacted, $C_3H_5OC_3H_6C_8F_{17}$, respectively.

Example 3

Hydrosilation of $C_3H_5C_8F_{17}$ with $Me_2SiHCl$ to give $C_8F_{17}C_3H_6Me_2SiCl$ $C_3H_5C_8F_{17}$ (113.0 g, 0.25 mol) and chloroplatinic acid solution in isopropanol (0.1 mL, ~10 ppm) were charged to a nitrogen flushed 250 mL round bottom flask equipped with a heating mantle, condenser, addition funnel, thermometer, magnetic stirrer, and nitrogen inlet. The mixture was stirred and heated to 75° C., at which time the heating mantle was removed and $Me_2SiHCl$ was added dropwise by addition funnel. The temperature decreased to 70° C., and the mixture began refluxing. The temperature of the mixture was controlled by the addition rate of $Me_2SiHCl$, and maintained between about 70° C. and 80° C. Once the addition was complete (30 minutes), heating was reapplied and the mixture stirred at 75° C. for one hour. The reaction mixture was then stripped of volatile components (rotary evaporator, 70° C., 1 mm Hg) to yield a light tan crystalline solid, identified as $C_8F_{17}C_3H_6Me_2SiCl$.

Example 4

Hydrolysis and condensation of $C_8F_{17}C_3H_6Me_2SiCl$ to yield $(C_8F_{17}C_3H_6Me_2Si)_2O$ $C_8F_{17}C_3H_6Me_2SiCl$ (20 g, 0.036 mol) in isopropyl ether (50 mL) was added dropwise to a vigorously stirred solution of concentrated HCl (3 g), H₂O (20 mL) and isopropyl ether (150 mL) in nitrogen flushed 500 mL round bottom flask equipped with a heating mantle, condenser, addition funnel, thermometer, magnetic stirrer, and nitrogen inlet. A slight exotherm was noted during the addition. The mixture was then stirred at ambient temperature 2 h, then heated to 65° C. for a total of 72 hours. Analysis indicated 95% conversion to $(C_8F_{17}C_3H_6Me_2Si)_2O$.

Example 5

Spreading of Methyl Soyate with $Me_3SiOMeSi(C_3H_6C_8F_{17})OSiMe_3$

Solutions of 5%, 1%, and 0.1% $Me_3SiOMeSi(C_3H_6C_8Fl_7)OSiMe_3$ (C-8PT) and 5% $Me_3SiOMeSi(C_3H_6OC_3H_6C_8F_{17})OSiMe_3$ (C-8PAET) in methylated soybean oil (methyl soyate) were prepared, and 10 μL samples were applied to overhead transparencies (polyester film surface). The spreading area (in cm²) of each droplet was measured over time, and the results were compared to neat methyl soyate and a solution containing 95% methyl soyate and 5% Silwet® 560 (Witco, Organo Silicones Group), a commercial oil spreading surfactant. The data are summarized in Table 1 and FIG. 1.

TABLE 1

Spreading Behavior of Fluoroalkyl Trisiloxanes at Various Concentrations in Methyl Soyate

| Time (hours) | Neat Methyl Soyate | 0.1% C-8PT | 1% C-8PT | 5% C-8PT | 5% C-8PAET | 5% Silwet® 560 |
|---|---|---|---|---|---|---|
| 0 | 0.07 | 0.07 | 0.07 | 0.07 | 0.07 | 0.07 |
| 1.5 | 3.80 | 5.30 | 40.70 | 76.90 | 63.39 | 4.49 |
| 4 | 4.91 | 4.91 | 80.72 | 179.57 | 120.97 | 23.75 |

C-8PT is a C-8 propene derivative corresponding to Formula (II) wherein a=3, b=0, c=0, and d=8; and C-8PAET is a C-8 propene allyl ether derivative corresponding to Formula (II) wherein a=3, b=1, c=3, and d=8.

It is clear from the above data that the inclusion of a small percentage of the fluoroalkyltrisiloxane provides a tremendous advantage in the spreading ability of the methyl soyate. In addition, the fluoroalkyltrisil-xanes clearly outperform a characteristic oil-spreading surfactant (Silwet® 560, Witco, Organo Silicones Group), allowing one to decrease the concentration 50 fold and achieve the same spreading activity.

We claim:

1. A fluoroalkylsilsiloxane corresponding to the formula (1):

$$R_x\diagdown_{Si}\diagup_{Me_{(3-x)}} \left[ \begin{array}{c} R_y \\ | \\ OSi \\ | \\ Me_{2-y} \end{array} \right]_z OSi\diagup^{R_x}_{Me_{(3-x)}} \quad (I)$$

wherein x is 0 to 3, y is 0,1 or 2; z is 0 or 1; x+y>0, and R has the formula $—C_aH_{2a}—O_b—C_cH_{2c}—C_dF_{2d+1}$ in which a is 2–4, b is 0 or 1, c is 0–8 and d is 4–12.

2. A fluoroalkyltrisiloxane of claim 1 corresponding to the formula:

$$Me_3Si\diagdown_O\diagup^R\diagdown_{Si}\diagup^{Me}\diagdown_O\diagup SiMe_3$$

wherein R has the formula $—C_aH_{2a}—O_b—C_cH_{2c}—C_dF_{2d+1}$ in which a is 2–4, b is 0 or 1, c is 2–3 and 4–12.

3. A fluoroalkyldisifoxane of claim 1 corresponding to formula:

$$Me_2Si\diagdown_O\diagup^{R\quad R}_{\ |\quad |}SiMe_2$$

wherein R has the formula $—C_aH_{2a}—O_b—C_cH_{2c}—C_dF_{2d+1}$ in which a is 2–4, b is 0 or 1, c is 2–3 and d is 4–12.

4. composition comprising 0.1% to 99.9% of a fluoroalkylsiloxane according to claim 1 and 99.9% to 0.1% of a vegetable, animal or paraffinic oil.

5. A composition according to claim 4 further comprising about 1% by weight to about 50% by weight of a nonionic surfactant.

6. A composition according to claim 4 comprising less than 20% of fluoroalkylsiloxane and more than 80% of vegetable, animal or paraffinic oil.

7. A composition according to claim 6 further comprising about 1% by weight to about 50% by weight of a nonionic surfactant.

8. A composition according to claim 6 wherein the vegetable oil is an esterified seed oil.

9. A composition according to claim 6 where the fluoroalkylsiloxane is a fluoroalkyltrisiloxane corresponding to formula:

$$Me_3Si\diagdown_O\diagup^R\diagdown_{Si}\diagup^{Me}\diagdown_O\diagup SiMe_3$$

wherein R has the formula $C_aH_{2a}—O_b—C_cH_{2c}—C_dF_{2d+1}$ in which a is 2–4, b is 0 or 1 c is 2–3 and d is 4–12 and the oil is a vegetable oil.

10. A process for enhancing the spreading of vegetable, animal or paraffinic oil by incorporating therein a fluoroalkylsiloxane according to claim 1.

11. A process for enhancing the spreading of vegetable, animal or paraffinic oil by incorporating therein a fluoroalkylsiloxane according to claim 2.

12. A process for enhancing the spreading of vegetable, animal or paraffinic oil by incorporating therein a fluoroalkylsiloxane according to claim 3.

13. A process for enhancing the spreading of vegetable, animal or paraffinic oil by incorporating therein a composition according to claim 4.

14. A process for enhancing the spreading of vegetable, animal or paraffinic oil by incorporating therein a composition according to claim 5.

15. A process for enhancing the spreading of vegetable, animal or paraffinic oil by incorporating therein a composition according to claim 6.

16. A process for improving the efficacy of an oil soluble pesticide comprising adding thereto a fluoroalkylsiloxane according to claim 1.

17. A process for improving the efficacy of an oil soluble pesticide comprising adding thereto a fluoroalkylsiloxane according to claim 2.

18. A process for improving the efficacy of an oil soluble pesticide comprising adding thereto a fluoroalkylsiloxane according to claim 3.

19. A process for improving the efficacy of an oil soluble pesticide comprising adding thereto a composition according to claim 4.

20. A process for improving the efficacy of an oil soluble pesticide comprising adding thereto a composition according to claim 5.

21. A process for improving the efficacy of an oil soluble pesticide comprising adding thereto a composition according to claim 6.

22. process for treating a plant or arthropod with an oil-containing composition, comprising applying to a plant or arthropod a composition comprising from about 0.1% by weight to about 99.9% by weight of an oil and about 99.9% by weight to about 0.1% by weight of a fluoroalkylsiloxane according to claim 1.

23. A process for treating a plant or arthropod with an oil-containing composition, comprising applying to a plant or arthropod a composition comprising from about 0.1% by weight to about 99.9% by weight of an oil and about 99.9% by weight to about 0.1% by weight of a fluoroalkylsiloxane according to claim 2.

24. A process for treating a plant or arthropod with an oil-containing composition, comprising applying to a plant or arthropod a composition comprising from about 0.1% by weight to about 99.9% by weight of an oil and about 99.9% by about 0.1% by weight of a fluoroalkylsiloxane according to claim 3.

25. A process for treating a plant or arthropod with an oil-containing composition, comprising applying to a plant or arthropod a composition according to claim 5.

26. A process for treating a plant or arthropod with an oil-containing composition, comprising applying to a plant or arthropod a composition according to claim 6.

27. A fluoroalkylsiloxane according to claim 1 wherein a is 3 to 4.

28. A fluoroalkylsiloxane according to claim 1 wherein b is 1.

29. A fluoroalkylsiloxane according to claim 1 wherein z is 1 and y=0.

* * * * *